United States Patent [19]

Hinkle et al.

[11] Patent Number: 4,843,077

[45] Date of Patent: Jun. 27, 1989

[54] ISOQUINOLINE DERIVATIVES HAVING RENAL VASODILATING PROPERTIES AND/OR CARDIOTONIC PROPERTIES AND/OR PHOSPHODIESTERASE INHIBITING PROPERTIES

[75] Inventors: Jeffery S. Hinkle, Pennington; O. William Lever, Jr., Skillman, both of N.J.

[73] Assignee: Ortho Pharmaceutical Corporation, Raritan, N.J.

[21] Appl. No.: 59,698

[22] Filed: Jun. 9, 1987

[51] Int. Cl.$^4$ .................. A61K 31/495; C07D 401/06
[52] U.S. Cl. .................................... 514/253; 514/252; 514/291; 514/309; 514/310; 544/361; 544/363; 546/90; 546/141; 546/143
[58] Field of Search ............... 544/363, 361; 546/141, 546/143, 90; 514/252, 253, 309, 310, 291

[56] References Cited

U.S. PATENT DOCUMENTS

| | | | |
|---|---|---|---|
| 3,247,212 | 4/1966 | Johnson | 546/141 |
| 3,930,837 | 1/1976 | Serban | 546/141 |
| 4,590,273 | 5/1986 | Konz et al. | 544/363 |

OTHER PUBLICATIONS

Sawanishi, et al., "Chemical Abstracts", vol. 101, 1984, col. 101:151239q.

*Primary Examiner*—Glennon H. Hollrah
*Assistant Examiner*—James H. Turnipseed
*Attorney, Agent, or Firm*—Benjamin F. Lambert

[57] ABSTRACT

Isoquinoline derivatives of compounds of the general formula

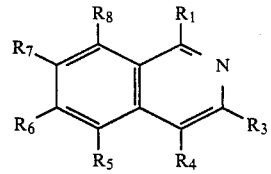

that exhibit cardiotonic and/or phosphodiesterase fraction III inhibiting properties and/or renal vasodilating are pharmacologically active in the treatment of cardiac conditions. Methods for synthesizing and using the compounds are described.

14 Claims, No Drawings

ISOQUINOLINE DERIVATIVES HAVING RENAL VASODILATING PROPERTIES AND/OR CARDIOTONIC PROPERTIES AND/OR PHOSPHODIESTERASE INHIBITING PROPERTIES

Description

1. Technical Field

The present invention relates to novel isoquinoline derivatives that exhibit renal vasodilating activity and/or cardiotonic and/or phosphodiesterase fraction III inhibiting properties, as well as methods for synthesis and utility of these compounds.

2. Background

Vasodilating agents produce a relaxation of the muscles of blood vessels that correspondingly enlarges the blood vessel passage, reduces resistance to blood flow and lowers blood pressure. As a result, more blood reaches the tissues. Examples of such agents include nitroglycerin, hydralazine and the like. Renal vasodilators produce a relaxation of blood vessels that are associated with the kidneys.

Compounds that exhibit cardiotonic properties cause cardiac muscle to pump more forcefully and effectively (a positive inotropic effect) and are often used to treat heart failure. Digitalis is one of the most frequently used cardiotonic agents; other examples include ouabain and strophanthidin.

Phosphodiesterases convert c-AMP (cyclic adenosine monophosphate) to 5'-AMP. Compounds that inhibit phosphodiesterase activity and its breakdown of c-AMP therefore provide enhanced levels of c-AMP. Cardiac phosphodiesterase fraction III is one example of a biologically active phosphodiesterase.

A number of compounds that are structurally related to the isoquinolines of this invention have been reported in the literature.

U.S. Pat. Nos. 3,798,225, 3,910,927 and 4,015,006 to Kreighbaum et al. (Mead Johnson & Co.) relate to 2-substituted-3(2H)-isoquinolones and 2-substituted-3-alkoxyisoquinolines that are reported to have hypotensive and peripheral vasodilating properties upon oral administration. The patents relate in particular to 1-benzyl derivatives of the above compounds.

The 3-hydroxy-4-nitroisoquinoline compounds used as starting materials in this invention are prepared according to the procedures described in our copending application Nos. 871,967 filed on June 9, 1986 and 882,655 filed on July 7, 1986, now U.S. Pat. No. 4,714,705, all of said procedures being incorporated herein by reference. For example, the starting material 3-hydroxy-6,7-dimethoxy-1-methyl-4-nitroisoquinoline may be prepared by the nitration of 3-hydroxy-6,7-dimethoxy-1-methyisoquinoline [which has been reported along with the corresponding 3-ethoxy and 3-acetoxy derivatives by Bentley et al., *J. Chem. Soc.*, 1763 (1952); Dorofeenko et al., *USSR Author's certificate No.* 207,921, CA, 69,52003x (1967); and D. Evans et al., *J. Chem. Soc. (B)*, 590 (1967)].

1-Phenylisoquinoline derivatives are described in German Offenlegunschrift No. DE-3,227,741 which issued to Hoechst AG. The compounds are reported to exhibit antidepressant activity. U.S. Pat. Nos. 4,282,222 and 4,282,223 to Bartmann et al. (assigned to Hoechst AG) describe isoquinolines including 3-piperidino, 3-piperazino, and 3-piperazino N-substituted derivatives that are reported to exhibit antidepresssant activity.

U.S. Pat. No. 3,870,721 to Archibald et al. relates to 4-alkanoylamino isoquinolinediones and 3-alkanoyloxy-4-alkanoylamino isoquinolones. A representative isoquinolinedione reported to inhibit platelet aggregation is 4-acetamido-1,2,3,4-tetrahydro-1,3-isoquinolinedione.

Belgian patent No. 875797-A to Rhone-Poulenc describes 4-imidazoylamino-isoquinolines that are reported as antihypertensives.

DETAILED DESCRIPTION OF THE INVENTION

Isoquinoline derivatives bearing a nitrogen substituent at C-4 and an oxygen radical, a nitrogen radical or a sulfur radical substituent at C-3, pharmaceutical compositions containing any such isoquinoline derivatives as an active ingredient, methods of treating a mammal exhibiting a cardiac condition, and methods for synthesizing the present compounds are contemplated.

The compounds of this invention have structural formula I:

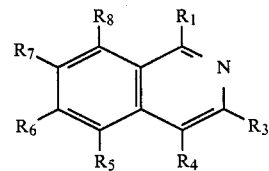

wherein $R_1$ is a radical selected from the group consisting of hydrogen, lower alkyl, cycloalkyl, aryl, arylalkyl and halogen-substituted radicals thereof;

$R_3$ is hydrazino, aryl hydrazino, lower alkyl hydrazino or an amino radical of the formula NR'R'' wherein R' and R'' are independently selected from hydrogen, acyl, lower alkyl, aminolower alkyl, lower alkylaminolower alkyl, lower dialkylaminolower alkyl, cycloalkyl, arylalkyl, aryl, lower alkenyl, lower alkynyl, arylalkyl, substituted arylalkyl, imidazolyl lower alkyl, arylpiperazinyl lower alkyl, substituted arylpiperazinyl lower alkyl, or when taken together may form a ring containing the nitrogen atom, such as an aroylpiperidinyl, substituted aroylpiperidinyl, diarylalkylidinylpiperidinyl, substituted diarylalkyldinylpiperidinyl, arylpiperazinyl arylalkylipiperazinyl and a diarylalkylpiperazinyl ring system; or a sulfur radical of formula SR''' in which R''' is lower alkyl, cycloalkyl, aryl or arylalkyl;

$R_4$ is a nitrogen substituent selected from the group consisting of nitro, nitroso, an amino radical of the formula NR'R'' wherein R' and R'' are as already defined, an acylamino radical of the formula NR'COR'' wherein R' and R'' are as already defined; a urea radical of formula NHCONR'R'' wherein R' and R'' are as already defined; or a radical of formula $N(CONHR')_2$ wherein R' is as already defined;

$R_5$, $R_6$, $R_7$, and $R_8$ may be independently selected from the group consisting of hydrogen, halogen, hydroxy, acyloxy and lower alkoxy; and $R_5$ and $R_6$, $R_6$ and $R_7$ or $R_7$ and $R_8$ when taken together may form a ring such as a methylenedioxy ring.

Exemplary compounds of the present invention whose structures conform to the above formula are listed in Table 1, below.

Also contemplated are pharmaceutically acceptable salts of a compound of this invention. Any conventional pharmaceutically acceptable salt can be used. Among the salts that can be prepared are acid addition salts prepared from organic and inorganic acids such as, for example, hydrochloric acid, hydrobromic acid, phosphoric acid, hypophosphoric acid, methanesulfonic acid, P-toluenesulfonic acid and sulfuric acid.

As used herein the term "lower alkyl" indicates a branched or straight chain hydrocarbon having 1 to about 8 carbon atoms, and particularly 1 to about 4 carbon atoms. Lower alkyl radicals include, for example, methyl, ethyl, propyl, isopropyl, n-butyl, sec-butyl, t-butyl, n-pentyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, 1-octyl, 2-octyl, and the like. The term "cycloalkyl" indicates a cyclic alkyl group having 3 to about 7 carbon atoms. The term "lower alkenyl" indicates a branched or straight chain hydrocarbon having about 3-5 carbon atoms such as 2-butenyl, 3-butenyl, allyl and isopentenyl, for example. The term "lower alkynyl" indicates a branched or straight chain hydrocarbon having 2-5 carbon atoms such as acetylenyl, 1-propynyl and 1-butynyl.

The term "aryl", as used herein alone or in combination with other terms, indicates aromatic hydrocarbon groups, such as phenyl or napthyl groups, which can be unsubstituted or substituted with one or more groups selected from lower alkyl radicals, halo lower alkyl radicals, hydroxy, lower alkoxy, lower alkylthio, halogens, nitrile, nitro, amino, sulfonic acid derivatives, or carboxylic acid derivatives COX wherein X is hydroxy, lower alkoxy, or NR'R" wherein R' and R" independently may be hydrogen or as already defined, for example.

The term "arylalkyl" indicates a radical containing a lower alkyl group substituted with an aryl radical as defined above.

The phrase "halogen-substituted radical" indicates a lower alkyl or aryl group and a lower alkyl, aryl or lower alkoxy-substituted aryl that includes a halogen selected from chloro, bromo, iodo and fluoro.

The term "lower alkoxy" indicates a radical containing a lower alkyl or an arylalkyl group (as defined above) and an oxygen atom at the terminus. Examples include methoxy, ethoxy, isopropoxy, n-butoxy, benzyloxy, and the like.

The term "acyloxy" indicates a residue of an aliphatic carboxylic acid having 2-6 carbon atoms which is attached to an oxygen atom such as acetyloxy, propionyloxy, butyryloxy and the like. The term "acyl" indicates a residue of an aliphatic carboxylic acid having 2-6 carbon atoms such as acetyl, propionyl, butyryl and the like.

The preferred compounds of this invention include those compounds wherein $R_1$ is lower alkyl; $R_3$ is NR'R" or SR'''; $R_4$ is nitro, nitroso, NR'R", NR'COR", NHCONR'R" or N(CONHR')$_2$; and $R_5$, $R_6$, $R_7$ and $R_8$ are hydrogen, hydroxy, acyloxy and lower alkoxy.

A pharmaceutical composition that comprises an effective amount of an above-described isoquinoline derivative dispersed in a pharmaceutically acceptable carrier is also contemplated herein. The composition comprises a unit dosage of the isoquinoline derivative.

Isoquinoline derivatives of this invention have cardiotonic and/or renal vasodilating and/or phosphodiesterase inhibiting properties. In preferred practice, the isoquinoline derivative of the pharmaceutical composition is capable of producing the desired cardiovascular effect in the amount at which that isoquinoline derivative is present in the pharmaceutical composition when that composition is introduced as a unit dose into an appropriate mammal such as a laboratory rat.

The term "unit dosage" and its grammatical equivalents are used herein to refer to discrete units suitable for administration to human patients and to warm-blooded mammals. Each unit contains a predetermined effective amount of the active ingredient calculated to produce the desired cardiostimulating and/or vasodilating effect in association with the required physiologically tolerable carrier, e.g. a diluent or a vehicle.

The specification for the novel unit dosage forms of this invention are dictated by and are directly dependent upon (a) the unique characteristics of the active ingredient and (b) the limitations inherent in the art of compounding such an active ingredient for therapeutic use in humans and other mammals. Examples of suitable unit dosage forms in accord with this invention are tablets, capsules, pills, powder packets, granules, wafers, and the like, segregated multiples of any of the foregoing, along with liquid solutions, liquid suspensions, elixirs and aerosol suspensions.

The active ingredient is referred to herein as being dispersed in the carrier. Thus the dispersion formed can be a simple admixture, a non-settling dispersion as in the case of certain emulsions or an ultimate dispersion, a true solution. In such compositons, the active ingredient is ordinarily present in an amount of at least about 0.5 percent by weight based on the total weight of the composition to about 90 percent by weight.

The effective amount of active ingredient that is administered in vivo depends on the age and weight of the mammal treated, the particular condition to be treated, the frequency of administration, and the route of administration. Exemplary unit doses can contain about 0.01 to about 100 milligrams per kilogram of body weight, more preferably about 0.1 to 20 milligrams per kilogram of body weight. The human adult dose is typically about 100 to about 500 milligrams daily, given as a single dose or in 3 or 4 divided doses. Veterinary dosages correspond to human dosages with the amounts administered being in proportion to the weight of the animal as compared to adult humans. It will be understood that the amount administered is determined by the physician or veterinarian in light of the relevant circumstances including the condition to be treated, the compound to be administered and the route of administration. Therefore, the foregoing dosage ranges are not intended to limit the scope of this invention in any way.

Pharmaceutically acceptable carriers are those well known in the art. The carrier may take a wide variety of forms depending on the form of preparation desired for administration, e.g., intravenous, oral or parenteral.

Liquid compositions include liquid phases in addition to or with the exclusion of water. Exemplary of such liquid phases are glycerin and vegetable oils including peanut oil and cottonseed oil.

Suitable solid carriers (diluents) include those materials usually used in the manufacture of pills, capsules or tablets, and include cornstarch, lactose, dicalcium phosphate, thickeners such as tragacanth and methylcellulose U.S.P., finely divided silica, polyvinylpyrrolidinone, magnesium stearate and the like. Antioxidants such as methylparaben and propylparaben can be present in both liquid and solid compositions, as can sweeteners such as cane sugar, beet sugar, sodium saccharin, sodium cyclamate and the dipeptide methyl ester sweetner sold under the trademark NUTRASWEET (aspartame) by G. D. Searle Co., Skokie, Il.

Methods for stimulating cardiac contractions, increasing contractile force of cardiac muscle and/or dilating renal vasculature in a mammal are also contemplated. The methods comprise administering to that mammal a unit dose of a pharmaceutical composition that includes an effective amount of an active ingredient that is an aforementioned isoquinoline derivative dispersed in a pharmaceutically acceptable carrier.

The pharmaceutical composition can be administered orally, by injection, by inhalation (for example, in the form of an aerosol, micropulverized powder or nebulized solution) or by any other means well known in the art.

Inasmuch as a pharmaceutical composition can be administered 2 or more times daily, the methods include the serial administration of the pharmaceutical composition into the treated mammal over a given time period.

Methods for synthesizing the particular isoquinoline derivatives of this invention are other aspects of the present invention.

The following examples describe the invention in greater particularity and are intended to be a way of illustrating but not limiting the invention.

METHODS OF PREPARATION

The various isoquinoline derivatives of this invention can be prepared by one of the following general methods.

The starting materials for the various compounds of this invention are isoquinoline compounds I wherein $R_1$, and $R_5-R_8$ are as already defined, $R_3$ is OH or $OSO_2R'''$ wherein R'' is as already defined and $R_4$ is $NO_2$, and are prepared according to the processes described in our co-pending applications Ser. No. 871,967 filed on June 9, 1986 and Ser. No. 882,655 filed on July 7, 1986, all of said processes being incorporated herein by reference.

The various 3-sulfonyloxy derivatives I wherein $R_3$ is $OSO_2R'''$ and R''', $R_1$, and $R_4-R_8$ are as already defined, are prepared by treating the corresponding isoquinoline I wherein $R_3$ is OH with sulfonyl anhydrides or halides, either neat or in an organic solvent such as benzene, toluene etc., a chlorohydrocarbon or an ether such as diethyl ether, tetrahydrofuran or dioxane, at temperatures ranging from $-5°$ C. to reflux temperatures. The sulfonylation of 3-hydroxyisoquinolines with a sulfonyl halide or anhydride may be performed either with or without a metal derived base such as a metal hydride, hydroxide, carbonate etc., or an organic base such as triethylamine, pyridine, dialkylaniline and the like. A catalyst such as 4-dialkylamino pyridine may also be added.

The various 3-substituted isoquinolines I wherein $R_4$ is $NO_2$, $R_3$ is NR'R'', or SR''' and R', R'', R''', $R_1$, and $R_5-R_8$ are as already defined, are prepared by treating the isoquinoline I (wherein $R_3$ is $OSO_2R'''$, R''' as already defined) with the corresponding amines (HNR'R'') or thiols (HSR'''), either neat or in an organic solvent such as benzene, toluene etc., a chlorohydrocarbon or an ether such as diethyl ether, tetrahydrofuran or dioxane, or in aqueous mixtures or solutions of the above solvents, either with or without a base such as triethylamine, at temperatures ranging from 20° C. to reflux temperatures.

The 4-nitro or 4-nitroso derivatives I ($R_4$ is $NO_2$ or NO and $R_1$, $R_3$, and $R_5-R_8$ are as already defined) can be reduced by standard methods, for example by catalytic hydrogenation, to obtain 4-amino derivatives I wherein $R_4$ is $NH_2$.

Compounds I with functionalized 4-amino substituents (wherein $R_4$ is as already defined) can be obtained from the 4-amino compounds I (wherein $R_4$ is $NH_2$) by standard methods, such as treatment with acylating agents, for example acyl anhydrides or chlorides, to provide 4-acylamino derivatives, or treatment with isocyanates or carbamoyl halides to provide 4-NHCONR'R'' or 4-N(CONR'R'')$_2$ derivatives.

A list of compounds that correspond to the foregoing formula, their biological activities and experimental procedures for their preparation are included in the following discussion.

A series of isoquinoline derivatives that were synthesized according to the various methods of the present invention are listed in Table 1.

Having generally described the invention, a more complete understanding can be obtained by reference to the following Examples, which are included for illustrative purposes only and are not intended to be limiting.

BEST MODES OF CARRYING OUT THE INVENTION

In the following Examples, melting points (mp) were determined on a Thomas-Hoover apparatus, and the melting points reported herein are uncorrected. The infrared (IR) spectra were recorded on a Nicolet 5DXB FT-IR spectrophotometer and are expressed in $cm^{-1}$. Proton nuclear magnetic resonance ($^1$H NMR) spectra were obtained in the indicated solvent with tetramethylsilane (TMS) as the internal standard on a Varian FT-80A or Varian XL-400 spectrometer. The values are expressed in delta ($\delta$) units downfield from TMS. Mass spectra were obtained on a Finnigan MAT 8230 Double Focusing high resolution mass spectrometer. Elemental analyses were obtained on a Perkin Elmer 240C for C, H, and N, and at Atlantic Microlabs for other elements (S, halogen).

EXAMPLE 1

6.7-Dimethoxy-1-methyl-4-nitro-3-[(4-toluenesulfonyl)oxy]isoquinoline (1).

Triethylamine (2.1 mL, 2 eq) and N,N-dimethylaminopyridine (0.28 g, 0.3 eq) were added to a stirred slurry of 6,7-dimethoxy-1-methyl-4-nitroisoquinolin-3-ol (2.00 g, 7.57 mmol) in methylene chloride (100 mL) at room temperature under a nitrogen atmosphere. Then p-toluenesulfonyl chloride (1.80 g, 1.25 eq) was added and the slurry was stirred at room temperature under nitrogen for 2–8 hours. The mixture was washed with water (2×150 mL), 25% saturated aqueous sodium bicarbonate (1×150 mL), dried (MgSO$_4$) and the solvent evaporated in vacuo. The solid residue was purified by trituration from methylene chloride or by column chromatography on silica with methylene chloride as eluent (Rf=0.8 in 98:2 methylene chloride:methanol) to give 2.26 g (71%) of the product as a yellow solid:

mp 236°–238° C. (dec);

IR (KBr) 1617, 1599 $cm^{-1}$;

$^1$H NMR (CDCl$_3$) $\delta$ 7.96 (d, J=7.9 Hz, 2H), 7.35 (d, J=7.9 Hz, 2H), 7.22 (s, 1H), 7.12 (s, 1H), 4.03 (s, 3H), 3.99 (s, 3H), 2.82 (s, 3H), 2.48 (s, 3H); LRMS (DCI), m/z (rel. int.), 419 (MH+, 100), 248 (45).

Anal. Calcd. for $C_{19}H_{18}N_2O_7S$: C, 54.54; H, 4.34; N, 6.69; S, 7.66;

Found: C, 54.80; H, 4.28; N, 6.81; S, 7.62

EXAMPLE 2

3-(n-Butylamino)-6,7-dimethoxy-1-methyl-4-nitroisoquinoline (3).

An excess of n-butylamine (0.8 mL, 4 eq) was added to a stirred slurry of 6,7-dimethoxy-1-methyl-4-nitro-3-[(4-toluenesulfonyl)oxy]isoquinoline (1) (1.00 g, 2.39 mmol) in toluene (50 mL) and the mixture was heated to reflux overnight. After cooling to room temperature, the precipitate was removed via filtration, washed with toluene, and purified by column chromatography on silica with methylene chloride as eluent to give 0.52 g (68%) of the product as an orange powder:

mp 160°–161° C.;

IR (KBr) 1624, 1598, 1577, 1498 cm$^{-1}$;

$^1$H NMR (CDCl$_3$) δ 9.6–9.3 (br t, 1H; D$_2$O exchangeable), 8.53 (s, 1H), 7.16 (s, 1H), 4.03 (s, 3H), 3.96 (s, 3H), 3.75 (td, appears as q, J=6.4 Hz, 2H; collapses to t, J=6.9 Hz upon D$_2$O exhange), 2.78 (s, 3H), 1.9–1.2 (m, 4H), 0.98 (t, J=6.7 Hz, 3H);

LRMS (DCI), m/z (rel. int.), 320 (MH+, 100), 290 (34).

Anal. Calcd. for $C_{16}H_{21}N_3O_4$: C, 60.18; H, 6.63; N, 13.16; Found: C, 60.41; H, 6.92; N, 13.15.

EXAMPLE 3

6,7-Dimethoxy-1-methyl-3-(N,N-dimethyl)amino-4-nitroisoquinoline (13).

An excess of 40% aqueous dimethylamine was added to 6,7-dimethoxy-1-methyl-4-nitro-3-[(4-toluenesulfonyl)oxy]isoquinoline (1) (1% (1.00 g, 2.39 mmol) in toluene (50 mL) and the mixture was heated to reflux for 4–8 hours. The mixture was then cooled, washed with 1N HCl (2×75 ml), and the organic layer dried (MgSO$_4$), and the solvent was evaporated under reduced pressure. The residue was purified by column chromatography on silica with methylene cloride as the eluent to provide 0.69 g (99%) of the product as a red solid:

mp 170°–171° C.;

IR (KBr) 1621, 1585, 1504 cm$^{-1}$; $^1$H NMR (CDCL$_3$) δ 7.68 (s, 1H), 7.12 (s, 1H), 4.00 (s, 3H), 3.96 (s, 3H), 3.12 (s, 6H), 2.76 (s, 3H);

LRMS (DCI), m/z (rel. int.), 292 (MH+, 100).

Anal. Calcd. for $C_{14}H_{17}N_3O_4$: C, 57.72; H, 5.88; N, 14.42; Found: C, 57.91; H, 5.87; N, 14.20.

EXAMPLE 4

3-(n-Butylthio)-6,7-dimethoxy-1-methyl-4-nitroisoquinoline (23).

n-Butanethiol (0.78 mL, 3 eq), triethylamine (0.67 mL, 2 eq) and potassium carbonate (1.32 g, 4 eq) were added to a stirred suspension of 6,7-dimethoxy-1-methyl-4-nitro-3-[(4-toluenesulfonyl)oxy]isoquinoline (1) (1.00 g, 2.39 mmol) in toluene (50 mL). The mixture was heated to reflux for 3 days. The mixture was cooled to room temperature, filtered, and the solids washed with methylene chloride. The filtrate was evaporated under reduced pressure and the residue was purified by column chromatrography on silica with methylene chloride as eluent to provide 0.59 g (73%) of the product as a yellow solid:

mp 130°–132° C.;

IR (KBr) 1622, 1562, 1557 cm$^{-1}$;

$^1$H NMR (CDCl$_3$) δ 7.44 (s, 1H), 7.17 (s, H), 4.01 (s, 3H), 3.99 (s, 3H), 3.26 (t, J=7.2 Hz, 2H), 2.86 (s, 3H), 1.9–1.2, (m, 4H), 0.95 (t, J=6.7 Hz, 3H); LRMS (DCI), m/z (rel. int.), 337 (MH+, 100), 307 (96).

Anal. Calcd. For $C_{16}H_{20}N_2O_4S$: C,57.13;H,5.99;N,8.33;S,9.53; Found: C,56.92;H,6.15;N,8.21;S, 9.48

EXAMPLE 5

4-Amino-6,7-dimethoxy-3-(N,N-dimethyl)amino-1-methylisoquinoline (26). 6,7-Dimethoxy-3-(N,N-dimethyl)amino-1-methyl-4-nitroisoquinoline (13) (2.03 g, 6.97 mmol) was hydrogenated in methanol (250 mL) with 10% palladium on carbon (0.60 g) at room temperature under 40 psig hydrogen for 4–6 hours. After filtration to remove the catalyst, the solvent was evaported under reduced pressure and the residue was triturated with ether to provide 1.44 g (79%) of the product as a yellow to green solid:

mp 164°–165° C.;

IR (KBr) 1627, 1586, 1574, cm$^{-1}$;

$^1$H NMR (CDCl$_3$) δ 7.12 (s, 1H), 6.91 (s, 1H), 3.98 (s, 6H), 2.76 (s, 6H); LRMS (DCI), m/z (re. int.), 262 (MH$^{30}$, 80), 261 (M+, 100).

Anal. Calcd. for: $C_{14}H_{19}N_3O_2$: C, 64.35; H, 7.33; N, 16.08; Found: C, 63.98; H, 7.46; N, 15.73.

EXAMPLE 6

4-[1-(3-Allyl)ureido]-6,7-dimethoxy-1-methyl-3-[(N-phenyl)amino]isoquinoline (29).

Allylisocyanate (0.15 mL, 1.1 eq) was added to a solution of 4-amino-6,7-dimethoxy-1-methyl-3-[(N-phenyl)amino]isoquinoline (25) (0.50 g, 1.6 mmol) in methylene chloride (25 mL). The mixture was refluxed under nitrogen for 3 days. The precipitate which formed was collected by filtration and washed with methylene chloride to provide 0.44 g (69%) of the product as a colorless solid;

mp 365°–370° C. (dec);

IR (KBr) 1635, 1610, 1575 cm$^{-1}$; $^1$H NMR (DMSO-d$_6$) δ 7.89 (s, 1H), 7.83 (s, 1H), 7.49 (d, J=7.8 Hz, 2H), 7.28 (s, 1H), 7.22 (dd, appears as t, J=7.6 Hz, 2H), 7.19 (s, 1H) 6.82 (t, J=7.3 Hz, 1H), 6.48 (br t, 1H), 5.96–5.84 (m, 1H), 5.20 (dd, J$_1$=17.3 Hz, J$_2$=1.6 Hz, 1H), 5.06 (dd, J$_1$10.4 Hz, J$_2$=1.6 Hz, 1H), 3.91 (s, 3H), 3.88 (s, 3H), 3.75 (m, 2H), 2.76 (s, 3H); LRMS (DCI), m/z (rel. int.), 393 (MH$^{30}$, 40), 233 (100).

Anal. Calcd. for $C_{22}H_{24}N_4O_3$: C, 67.33; H, 6.16; N, 14.28; Found: C, 67.31; H, 6.17; N, 14.05.

EXAMPLE 7

4-[(N-Acetyl)amino]-6,7-dimethoxy-3-[(N,N-dimethyl)-amino]-1-methyl-isoquinoline (31).

Acetyl chloride (0.03 mL, 1.1 eq) was added to a stirred solution of 4-amino-6,7-dimethoxy-3-(N,N-dimethyl)-amino-1-methylisoquinoline (26) (0.09 g, 0.34 mmol) and triethylamine (0.06 mL, 1.2 eq) in methylene chloride (5 mL). The solution was then gently refluxed under nitrogen atmosphere for 3 hours. The resulting solution was passed through a silica gel column, eluted with methylene chloride, and the fractions with material at Rf 0.4 (98:2 methylene chloride:methanol) were evaporated under reduced pressure. Trituration of the residue with ether gave 0.07 g (67%) of the product as an off-white solid; mp 158 (coalesc.), 167°–168° C.;

IR (KBr) 1650, 1500 cm$^{-1}$;

$^1$H NMR (CDCl$_3$) δ 7.15 (s, 1H), 7.01 (s, 0.5H), 6.92 (s, 1H), 6.79 (s, 0.5H), 4.00 (s, 3H), 3.99 (s, 3H), 3.03 (s, 3H), 2.86 (s, 3H), 2.80 (s, 3H), 2.37 (s, 3H);

LRMS (DCI), m/z (rel. int.), 304 (MH$^+$, 100).

Anal. Calcd. for C$_{16}$H$_{21}$N$_3$O$_3$: C, 63.35; H, 6.98; N, 13.85; Found: C, 63.56; H, 7.11; N, 13.88.

RESULTS

A. Renal Vasodilating Activity

Goldberg et al., *J. Pharmacol. Exp. Ther.*, 163, 188 (1968), performed an investigation of the structural requirements for dopamine-like renal vasodilation of phenethylamines and apomorphine. The following procedure is a variation of the assay described in that report.

Adult mongrel dogs were anesthetized and surgically prepared for electromagnetic measurement of renal artery blood flow. A carotid artery was cannulated for measuring arterial blood pressure and drugs were administered intravenously or intraarterially (via the renal artery). Heart rate was monitored with a cardiotachometer. Renal vascular resistance was calcualted as the ratio of mean arterial blood pressure to renal artery blood flow. Dopamine was infused intravenously at 3 μg/kg/min for ten minutes (at an infusion rate of about 1 ml/min) to determine responsiveness of each dog to renal dopamine receptor stimulation. Cumulative dose-response data were obtained by infusing a compound of this invention at progressively increasing (usually three-fold) infusion rates, each dose being infused for five minutes. The maximum percent change from pre-drug control in renal artery blood flow (or in renal vascular resistance) was determined for each infusion dose.

Representative data for the isoquinoline derivatives of this invention are summarized in Table 2. RBF, RVR, MABP, and HR values are percent changes in renal blood flow, renal vascular resistance, mean arterial blood pressure, and heart rate, respectively, relative to control values.

B. Cardiotonic Activity

The acute in vivo cardiotonic activity of compounds prepared according to the present invention was determined according to a modification of the procedure described by Alousi et al., *Circ. Res.*, 45, 666 (1979).

In particular, adult mongrel dogs were anesthetized with sodium pentobarbital and were artificially respired. Arterial pressure was monitored via a femoral artery, and the pulse pressure was used to trigger a cardiotachometer for heart rate. Left ventricular pressure was determined with a Millar catheter, and dP/dT (the change in ventricular pressure with time) was derived. Cardiac output was determined by measuring ascending aortic blood flow with an electromagnetic flow probe, and myocardial contractile foorce was measured with a Walton Brodie strain gauge sutured to the right ventricle. Lead II EKG was also recorded.

A standard dose (10 μg/kg/min) of dopamine was administered to assess myocardial responsiveness.

Compounds of the invention were administered by intravenous infusion and the effects on cardiovascular parameters were determined. The total amount of each compound that was administered is shown in Table 3.

Dose related effects of the test compound on heart rate (HR), maximum change in left ventricular pressure with time (dP/dT), percent change in cardiac force (CF) and the change in mean arterial blood pressure (MABP) were compared to pretreatment control values and expressed as a percent change. Data for compounds of this invention are summarized in Table 3.

C. Inhibition of Phosohodiesterase Fraction III Activity

Thompson et al. described a cyclic nucleotide phosphodiesterase assay in *Advances in Cyclic Nucleotide Research*, Brooker et al., eds., 10, 69–92 (1979). The following procedure is based on that published assay and measures the ability of compounds to inhibit cyclic nucleotide phosphodiesterase which is an enzyme that converts either cyclic AMP or cyclic GMP to the non-cyclized AMP or GMP, respectively.

Compounds were tested at various concentrations in the presence of cyclic AMP (0.01–1.0 micromolar containing 0.2 microCuries $^3$H-cyclic AMP), cyclic nucleotide phosphodiesterase, and 0.05 M Tris-Cl buffer (pH 7.4, containing 5 mM magnesium chloride). After a specified time, the reaction was stopped by heating to 100° C. for one minute. After cooling, 0.01 ml of a solution containing snake venom (1 mg/ml) was added and the reaction was allowed to proceed for 30 minutes. Termination of this reaction was accomplished by addition of 1.0 ml of 33 percent DOWEX AGlx8 resin slurry (Dow Chemical Co., Midland, Mich.) to separate the product from the unconverted substrate. An aliquot was removed from the supernatant and analyzed by liquid scintillation spectrometry.

The fraction III enzyme was isolated as an isozyme from the crude canine heart homogenate by ion exchange chromatography. The enzyme activity was designated as fraction III since it is the third and last phosphodiesterase activity to be eluted from the chromatography column. The fraction III enzyme has a relatively high affinity and specificity for cyclic AMP.

Inhibition data is presented as the IC$_{50}$ value, the concentration (in micromoles) of a compound that was required to inhibit 50 percent of the cyclic nucleotide phosphodiesterase activity. Data for isoquinolines of this invention are summarized in Table 4.

TABLE 1

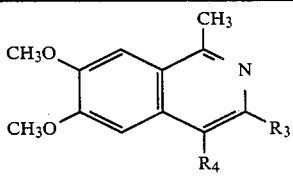

| Cmpd | Example | R$_3$ | R$_4$ | MP, deg. C |
|------|---------|-------|-------|------------|
| 2 | 3 | NHMe | NO$_2$ | 233–234 |

TABLE 1-continued

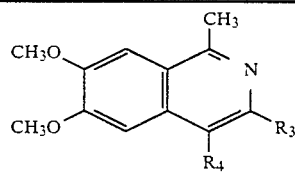

| Cmpd | Example | R₃ | R₄ | MP. deg. C |
|---|---|---|---|---|
| 3 | 2 | NH(nBu) | NO₂ | 160–161 |
| 4 | 2 | NHCH₂Ph | NO₂ | 140–141 |
| 5 | 2 | NHCH₂CH₂[3,4-(OMe)₂]C₆H₄ | NO₂ | 180–182 |
| 6 | 2 | NHCH₂CH₂NEt₂ | NO₂ | 148–150 |
| 7 | 2 | NHCH₂CH₂CH₂(1H—imidazol-1-yl) | NO₂ | 176–178 |
| 8 | 2 | NHCH₂CH₂N[CH₂CH₂]₂N(2-OMe)C₆H₄ | NO₂ | 190–192 |
| 9 | 2 | NH(iPr) | NO₂ | 219–220 |
| 10 | 2 | NHCH(Me)CH₂CH₂CH₂NEt₂ | NO₂ | 85–87 |
| 11 | 2 | NHCH[CH₂CH₂]₂NCH₂Ph | NO₂ | 188–189 |
| 12 | 2 | NHPh | NO₂ | 200–201 |
| 13 | 3 | NMe₂ | NO₂ | 170–171 |
| 14 | 2 | N(Me)Et | NO₂ | 135–136 |
| 15 | 3 | NEt₂ | NO₂ | 130–131 |
| 16 | 2 | N(Et)CH₂CH₂NMe₂ | NO₂ | 81–82 |
| 17 | 2 | N(CH₂CH₂)₂CHCO(4-F)C₆H₄ | NO₂ | 193–195 |
| 18 | 2 | N(CH₂CH₂)₂C=C[(4-F)C₆H₄]₂ | NO₂ | 164–166 |
| 19 | 2 | N[CH₂CH₂]₂NPh | NO₂ | 179–181 |
| 20 | 2 | N(CH₂CH₂)₂NCHPh₂ | NO₂ | 187–188 |
| 21 | 2 | N(Me)Ph | NO₂ | 182–184 |
| 22 | 3 | NHNH₂ | NO₂ | 198–199 (d) |
| 23 | 4 | S(nBu) | NO₂ | 130–132 |
| 24 | 5 | NH(iPr) | NH₂ | 95–99 (d) |
| 25 | 5 | NHPh | NH₂ | 198–202 |
| 26 | 5 | NMe₂ | NH₂ | 164–165 |
| 27 | 6 | NHPh | NHCONH(nBu) | 194–196 (c) >375 (d) |
| 28 | 6 | NMe₂ | NHCONH(nBu) | 225–226 |
| 29 | 6 | NHPh | NHCONH(allyl) | 365–370 (d) |
| 30 | 6 | NMe₂ | NHCONH(allyl) | 238–240 (c), 258–264 (d) |
| 31 | 7 | NMe₂ | NHCOCH₃ | 158 (c), 167–168 |

(c) = coalescence
(d) = decomposition

TABLE 2

| Cmpd # | Dose, mpk iv | RBF | RVR | MABP | HR |
|---|---|---|---|---|---|
| 4 | 6.2 | 9 | −14 | −6 | −15 |
| 8 | 0.3 | 10 | −27 | −20 | −6 |
| 11 | 6.2 | 28 | −28 | −13 | −16 |
| 12 | 6.2 | 42 | −32 | −3 | 2 |
| 13 | 1.2 | 60 | −23 | 16 | 17 |
| 15 | 6.2 | 8 | −8 | 0 | 4 |
| 19 | 6.2 | 30 | −18 | 6 | −5 |
| 23 | 6.2 | 16 | −15 | −1 | 4 |
| 27 | 1.2 | 7 | 1 | 8 | −6 |
| 30 | 1.2 | 12 | −9 | 1 | 3 |

RBF is percent change in renal blood flow; RVR is percent change in renal vascular resistance; MABP is percent change in mean arterial blood pressure; HR is percent change in heart rate; all values are expressed as percent change relative to controls.

TABLE 3

| Cmpd # | Dose, mpk iv | CF | dP/dt | HR | MABP |
|---|---|---|---|---|---|
| 6 | 1.875 | 40 | 52 | −6 | 4 |
| 14 | 1.938 | 21 | 20 | 8 | 6 |
| 28 | 1.875 | 20 | 16 | 2 | 2 |

CF is percent change in cardiac force; dP/dT is the maximum percent change in left ventricular pressure with time; HR is percent change in heart rate; MABP is percent change in mean arterial blood pressure; all values are expressed as percent change relative to controls.

TABLE 4

| Cmpd # | IC₅₀ (uM) |
|---|---|
| 2 | 265 |
| 3 | 250 |
| 11 | 120 |
| 12 | 250 |
| 13 | 10 |
| 14 | 25 |
| 16 | 300 |
| 19 | 150 |
| 21 | 220 |
| 23 | 280 |
| 25 | 68 |
| 26 | 14 |
| 28 | 300 |
| 30 | 280 |

Methods of Preparing Starting Materials

The starting materials used to prepare the isoquinoline compounds of this invention can be prepared by one of the following general methods.

Method 1

In formula I when R₆ is an electron donating substituent, for example, a lower alkyl, lower alkoxy, halogen or acetamido radical, the compound can be prepared by either formylating (wherein R₁ is hydrogen) or acylating (wherein R₁ is lower alkyl or aryl) a phenyl compound of formula II wherein A is CN (phenylacetonitrile) or COOR [phenylacetic acid derivative in which R is hydrogen or lower alkyl] and R₅ and R₈ are

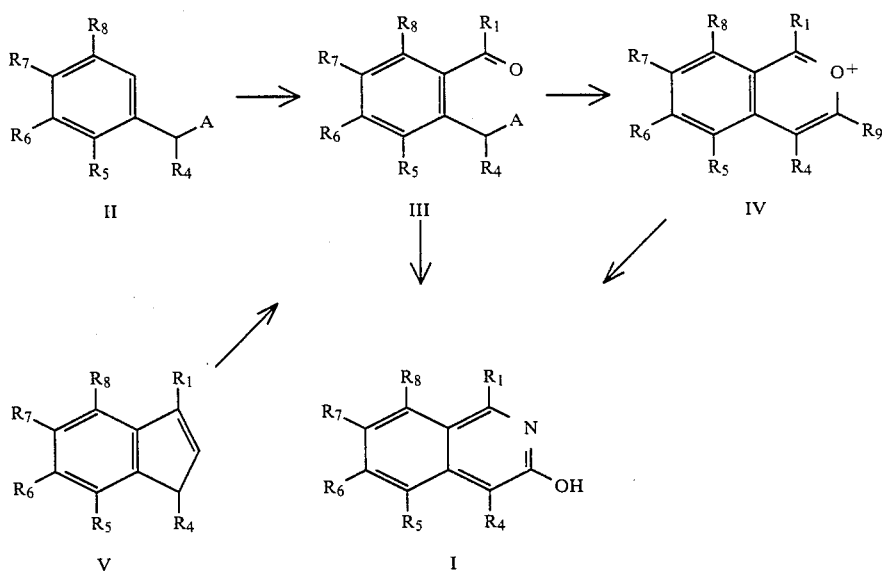

as already defined and $R_4$ is hydrogen.

Formylation of II to give the o-formyl derivative III (wherein $R_1$ is hydrogen) can be performed by electrophilic substitution with HCN or a metal cyanide salt and acid or with a formic acid derivative including, for example, $Cl_2CHOCH_3$, formamide, dimethylformamide and the like and a Lewis acid catalyst such as $ZnCl_2$, $SnCl_4$, $AlCl_3$, $ZrCl_4$, $TiCl_4$, $BF_3$ etherate, and the like. Acylation of II to provide O-acyl derivative III (where $R_1$ is lower alkyl or aryl) can be similarly effected under conventional Friedel-Crafts reaction conditions using either an acid chloride ($R_1COCl$), acid anhydride $[(R_1CO)_2O]$ or an acid ($R_1COOH$) and a Lewis acid catalyst, such as including $AlCl_3$, $ZrCl_4$, $TiCl_4$, $FeCl_3$, $ZnCl_2$, $SnCl_4$, $BF_3$ etherate, $HClO_4$, $(CF_3CO)_2O$, $CF_3SO_3H$, or polyphosphoric acid (PPA). The o-acylphenylacetic acid derivative III can also be prepared by other methods such as oxidative ring opening of an appropriately substituted 1-indene derivative (V).

The o-formyl or o-acyl derivative III can either be directly converted to the isoquinoline derivative I upon reaction with ammonium hydroxide, ammonia or an acid salt thereof including ammonium acetate, ammonium carbonate and the like.

Alternatively, the o-formyl or o-acyl derivative III can be first treated with a strong acid including, for example, perchloric acid, trifluoroacetic acid, trifluorosulfonic acid, boron trifluoride etherate and the like to form a 2-benzopyrylium salt IV wherein $R_9=OR$ (when A=COOR in II) or $NHCOR_1$ (when A=CN in II) having R and $R_1$ as described above. Treatment of the 2-benzopyrylium salt IV with ammonia or ammonium hydroxide in a solvent, for example, water, a lower alkanol such as ethanol, D-propanol or t-butanol, an ether such as diethyl ether or ethylene glycol diethyl ether, tetrahydrofuran (THF), a hydrocarbon such as benzene or toluene or a chlorohydrocarbon including methylene chloride, chloroform or carbon tetrachloride at zero degrees C. to about 150 degrees C. provides the isoquinolinol derivative I.

Method 2

Isoquinolinol compounds of the general formula I containing $R_7$ as an electron releasing group and $R_1$–$R_8$ (as defined above) can be prepared by the Pomeranz-Fritsch type cyclization of an appropriately substituted intermediate (VI) with an acid such as sulfuric acid, PPA, $BF_3$ etherate and the like.

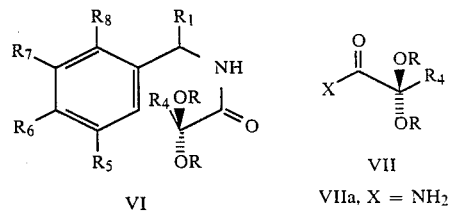

Compound VI can be prepared by reacting a benzylamine with acid derivative VII wherein X is halogen; OR and R are lower alkyl radicals and $R_4$ is as defined above. Alternatively, Compound VI can be prepared by displacing an appropriate benzyl halide by an amide anion derived from amide VIIa.

Method 3

3-Isoquinolinol compounds I wherein $R_4$ is nitro or nitroso can be prepared by electrophilic substitution at $C_4$ of Formula I (wherein $R_4$ is H). In particular, treatment of Compound I with fuming nitric acid in acetic acid, acetic anhydride and the like alone or in combination with ether, methylene chloride and the like provides the 4-nitro derivative; and treatment with $HNO_2$ [generated by combining sodium nitrite and an acid or an alkylnitrite and an acid or base] provides the 4-nitroso derivative.

The starting materials II IV are either known compounds or can be prepared from known compounds by methods known to those skilled in the art.

EXAMPLE A

3-Hydroxy-6,7-dimethoxy-1-methyl-4-nitroisoquinoline

3-Hydroxy-6,7-dimethoxy-1-methylisoquinoline (0.927 grams, 4.23 mmol) was dissolved in 60 ml glacial acetic acid by warming, and when the solution cooled to 15° C., a crystalline solid separated. To this mechanically stirred slurry were added 1.5 ml of a nitrating mixture (comprising 0.6 ml glacial acetic acid and 0.9 ml of 90 percent nitric acid) over a period of 15 minutes at 15° C. From the reaction mixture, a heavy yellow solid was isolated by filtration and washed with acetic acid. Alternatively, the reaction mixture was first quenched with 300 ml of water and the yellow solid was isolated by filtration, washed with water and dried in vacuo at 50° C. to provide 0.70 grams of Compound H (62.7% yield) having a melting point greater than 300° C.

$^1$H NMR (TFA): δ 3.23 (singlet, 3 H, 1-CH$_3$); δ 4.20 (singlet, 3 H, OCH$_3$); δ 4.32 (singlet, 3 H, OCH$_3$); δ 7.65 (singlet, 1 H, ArH); δ 8.70 (singlet, 1 H, ArH).

Mass spectrum: m/e 264 (M+)

Anal. Calculated for C$_{12}$H$_{12}$N$_2$O$_5$: C, 54.55; H, 4.58; N, 10.60; Found: C, 54.24; H, 4.65; N, 10.32.

The starting materials for the compounds of this invention are prepared from an appropriately substituted isoquinoline according to the method of Example A.

What is claimed is:

1. A compound of the formula:

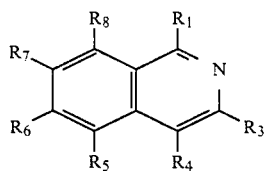

wherein

R$_1$ is selected from the group consisting of hydrogen, lower alkyl, cycloalkyl having 3–7 carbon atoms, phenyl, naphthyl, phenyl lower alkyl, naphthyl lower alkyl, and halogen-substituted radicals thereof;

R$_3$ is hydrazino, phenyl hydrazino, naphthyl hydrozino, lower alkyl hydrazino or NR'R" wherein R' and R" are independently selected from hydrogen, lower alkyl, amino lower alkyl, lower alkylamino lower alkyl, lower dialkylamino lower alkyl, cycloalkyl having 3–7 carbon atoms, phenyl, naphthyl, phenyl lower alkyl, naphthyl lower alkyl, C$_{3-5}$ alkenyl, C$_{2-5}$ alkynyl, substituted phenyl lower alkyl and naphthyl lower alkyl wherein the substituent is selected from lower alkyl, halo lower alkyl, hydroxy, lower alkoxy, lower alkylthio, halo, CN, NO$_2$, NH$_2$, sulfonic acid derivatives thereof and carboxylyic acid derivatives COX wherein X is hydroxy, lower alkoxy or NR' R" wherein R' and R" are as defined above, imidazolyl lower alkyl, phenylpiperazinyl lower alkyl, naphthyl piperazinyl lower alkyl, substituted phenyl piperazinyl lower alkyl and substituted naphthyl piperazinyl lower alkyl wherein the substituent is selected from lower alkyl, halo lower alkyl, hydroxy, lower alkoxy, lower alkylthio, halo, CN, NO$_2$, NH$_2$, sulfonic acid and carboxylic acid derivatives thereof, lower alkyl, phenyl alkyl piperidinyl, naphthyl alkyl piperidinyl, and benzoyl piperidinyl;

R$_4$ is selected from the group consisting of nitro, nitroso, an amino radical of the formula NR'R" wherein R' and R" are as defined above, NR"COR' wherein R' and R" independently are as defined above, N(CONHR')$_2$ wherein R' is as defined above, NHCONR'R" wherein R' and R" are as defined above;

R$_5$, R$_6$, R$_7$, and R$_8$ may be independently selected from the group consisting of hydrogen, halogen, hydroxy, cyloxy and lower alkoxy; and R$_5$ and R$_6$, R$_6$ and R$_7$ or R$_7$ and R$_8$ when taken together may form a methylenedioxy ring.

2. The compound of claim 1 wherein R$_1$ is lower alkyl; R$_3$ is NR'R"1 R$_5$, R$_6$, R$_7$ and R$_8$ are hydrogen, hydrOxy, acylOxy and lower alkoxy.

3. The compound of claim 1 which compound is 3-[1-[(2-diethylamino)ethyl]amino]-6,7-dimethoxy-1-methyl-4-nitroisoquinoline.

4. The compound of claim 1 which compound is 3-[[(1-benzyl)-4-piperidinyl]amino]-6,7-dimethoxy-1-methyl-4-nitroiosquinoline.

5. The compound of claim 1 which compound is 6,7-dimethoxy-1-methyl-4-nitro-3-(N-phenyl)amino-isoquinoline.

6. The compound of claim 1 which compound is selected from 6,7-dimethoxy-1-methyl-3-(N,N-dimethyl)amino-4-nitroisoquinoline and 3-[(N-ethyl-N-methyl)amino]-6,7-dimethoxy-1-methyl-4-nitroisoquinoline.

7. The compound of claim 1 which compound is selected from 6,7-dimethoxy-1-methyl-4-nitro-3-[1[-(4-phenyl)piperazinyl]]isoquinoline and 4-amino-6,7-dimethoxy-3-(N,N-dimeth)amino-1-methylisoquinoline.

8. A pharmaceutical composition comprising an effective amount of a compound according to claim 1 as the active ingredient dispersed in a pharmaceutically acceptable carrier.

9. The pharmaceutical composition according to claim 8 wherein said compound is capable of increasing the efficiency of cardiac contractions in the amount present in the composition when said composition is introduced into a mammal.

10. The pharmaceutical composition according to claim 8 wherein said compound is capable of increasing the contractile force of cardiac muscle in the amount present in the composition when said composition is introduced into a mammal.

11. The pharmaceutical composition according to claim 8 wherein said compound is capable of stimulating renal vasodilation in the amount present in the composition when said composition is introduced into a mammal.

12. The pharmaceutical composition according to claim 8 wherein said compound is capable of inhibiting the hydrolytic activity of phosphodiesterase fraction III in the amount present in the composition when said composition is introduced into a mammal.

13. A method for increasing the contractile force of cardiac muscle in a mammal comprising administering to said mammal a unit dose of the pharmaceutical composition according to claim 8.

14. A method for stimulating vasodilation in a mammal comprising administering to said mammal a unit dose of the pharmaceutical composition according to claim 8.

* * * * *

UNITED STATES PATENT AND TRADEMARK OFFICE
CERTIFICATE OF CORRECTION

PATENT NO. : 4,843,077

DATED : June 27, 1989

INVENTOR(S) : Jeffery S. Hinkle and William Lever, Jr.

It is certified that error appears in the above-identified patent and that said Letters Patent is hereby corrected as shown below:

Column 16, line 5 - cyloxy should be "acyloxy".

Column 16, line 9 - NR'R"1 should be NR'R",

Signed and Sealed this

Fifteenth Day of May, 1990

Attest:

HARRY F. MANBECK, JR.

*Attesting Officer*      *Commissioner of Patents and Trademarks*